(12) United States Patent
Matsumoto et al.

(10) Patent No.: US 8,248,241 B2
(45) Date of Patent: Aug. 21, 2012

(54) ASSEMBLY WORK SUPPORTING METHOD AND SYSTEM

(75) Inventors: Kazuhiko Matsumoto, Kawasaki (JP); Toshio Okochi, Musashino (JP); Kei Suzuki, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 784 days.

(21) Appl. No.: 12/314,131

(22) Filed: Dec. 4, 2008

(65) Prior Publication Data

US 2009/0160614 A1 Jun. 25, 2009

(30) Foreign Application Priority Data

Dec. 25, 2007 (JP) ................................ 2007-331323

(51) Int. Cl.
*G08B 13/14* (2006.01)
(52) U.S. Cl. .................. 340/572.1; 340/10.1; 340/572.8
(58) Field of Classification Search ................ 340/572.1
See application file for complete search history.

(56) References Cited

U.S. PATENT DOCUMENTS

| 6,502,009 | B1 * | 12/2002 | Parnell et al. ............... 700/200 |
| 7,441,320 | B2 * | 10/2008 | Hass et al. ..................... 29/593 |
| 2003/0081825 | A1 * | 5/2003 | Mitterholzer ................. 382/141 |
| 2004/0075559 | A1 * | 4/2004 | Brodine ...................... 340/572.1 |
| 2004/0085208 | A1 | 5/2004 | Fukuoka |
| 2004/0183683 | A1 | 9/2004 | Funahashi |
| 2007/0069909 | A1 * | 3/2007 | Pavlovic et al. .............. 340/687 |
| 2007/0080804 | A1 * | 4/2007 | Hirahara et al. .......... 340/572.1 |
| 2007/0102505 | A1 | 5/2007 | Yokota et al. |
| 2008/0048862 | A1 * | 2/2008 | Kritt et al. .................. 340/572.1 |
| 2009/0102610 | A1 * | 4/2009 | Lance .......................... 340/10.2 |

FOREIGN PATENT DOCUMENTS

| JP | 3565217 | 10/2002 |
| JP | 2004-287616 | 3/2003 |
| JP | 2005-157936 | 11/2003 |
| JP | 2006-268079 | 3/2005 |
| JP | 2007-151383 | 10/2006 |

* cited by examiner

*Primary Examiner* — George Bugg
*Assistant Examiner* — Kerri McNally
(74) *Attorney, Agent, or Firm* — Stites & Harbison, PLLC; Juan Carlos A. Marquez, Esq

(57) ABSTRACT

Detecting whether components are combined and coupled correctly in assembly work is performed by correct and simple operations. The proposed method includes reading a first IC tag attached to a joint part of a first component and a second IC tag attached to a joint part of a second component together in a manner of preventing collision and determining whether the first component and the second component are coupled correctly, based on information representing mating relations of IC tags memorized beforehand.

11 Claims, 14 Drawing Sheets

FIG. 5B

DRUG DB — MDB

| # | DRUG | WHERE IT IS | QUANTITY | POINTER TO DRUG IDs | |
|---|---|---|---|---|---|
| | | | | (START) | (END) |
| 1 | M1 | DRUG STORAGE 1 | 200cc | | |
| 2 | M1 | DRUG STORAGE 1 | 500cc | | |
| 3 | M2 | DRUG STORAGE 2 | 1mg | | |
| 4 | M2 | DRUG STORAGE 2 | 2mg | | |

| DRUG ID |
|---|
| M0010 |
| M0011 |
| M0012 |
| M0020 |
| M0021 |
| M0022 |
| |

MEDICAL STAFF DB — NDB

| # | NAME | FUNCTION | DEPARTMENT | ID |
|---|---|---|---|---|
| 1 | SATO ICHIRO | DOCTOR | INTERNAL MEDICINE | D001 |
| 2 | YOSHIDA JIRO | DOCTOR | SURGERY | D002 |
| 3 | SAITO TARO | NURSE | INTERNAL MEDICINE | N001 |
| 4 | ISHIDA HANAKO | NURSE | SURGERY | N002 |

PATIENT DB — PDB

| # | NAME | PATIENT ID | MEDICAL RECORD ID | PATIENT'S ROOM | ROOM ID | BED | BED ID |
|---|---|---|---|---|---|---|---|
| 1 | SATO YOSHIO | P001 | C001 | E | R004 | EB1 | B501 |
| 2 | SUZUKI KAZUKO | P002 | C008 | F | R005 | EB2 | B502 |

MEDICAL RECORD DB — RDB

| # | MEDICAL RECORD ID | POINTER TO MEDICAL RECORD CONTENT |
|---|---|---|
| 1 | C001 | |
| 2 | C002 | |

ORDER DB — ODB

| # | ORDER ID | MEDICAL RECORD ID | POINTER TO ORDER CONTENT |
|---|---|---|---|
| 1 | O001 | C002 | |
| 2 | O002 | C007 | |

FIG. 11
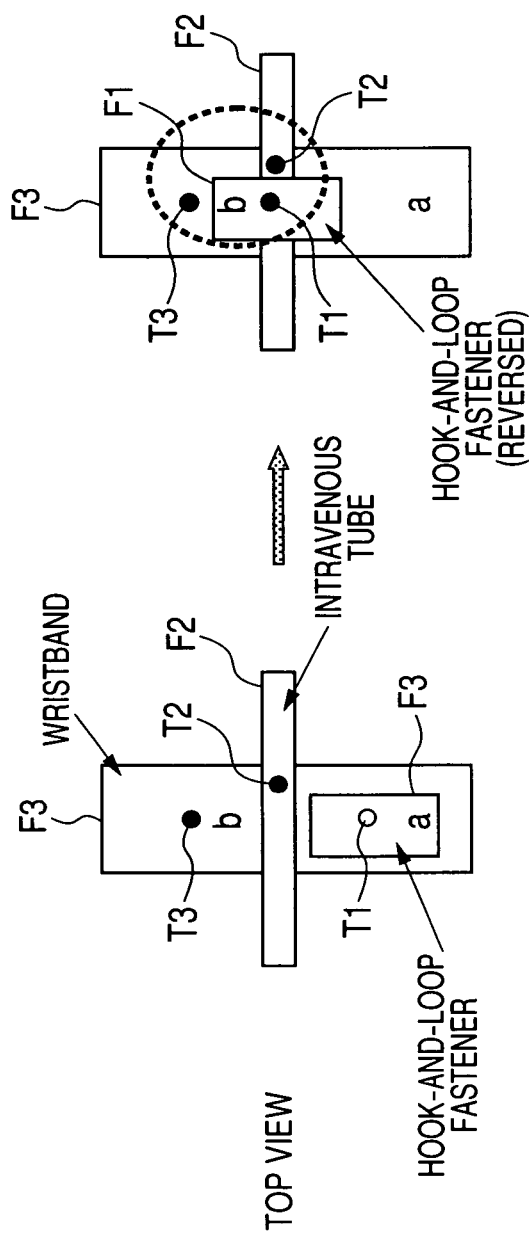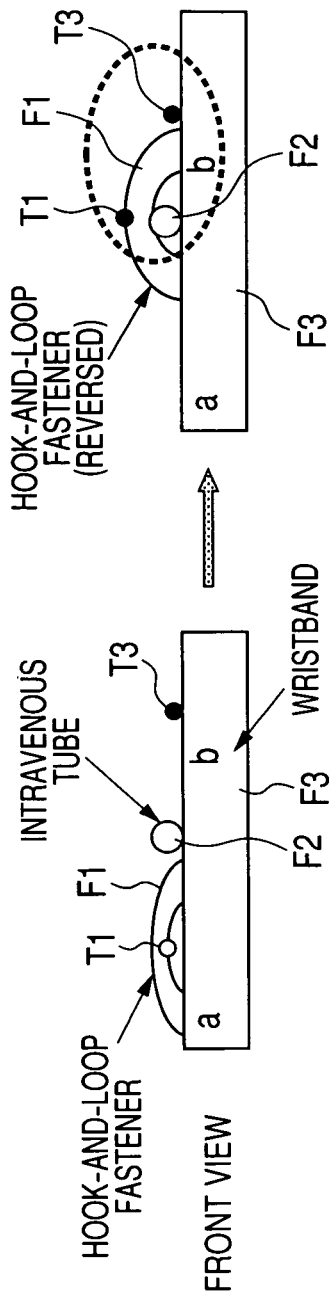

FIG. 12
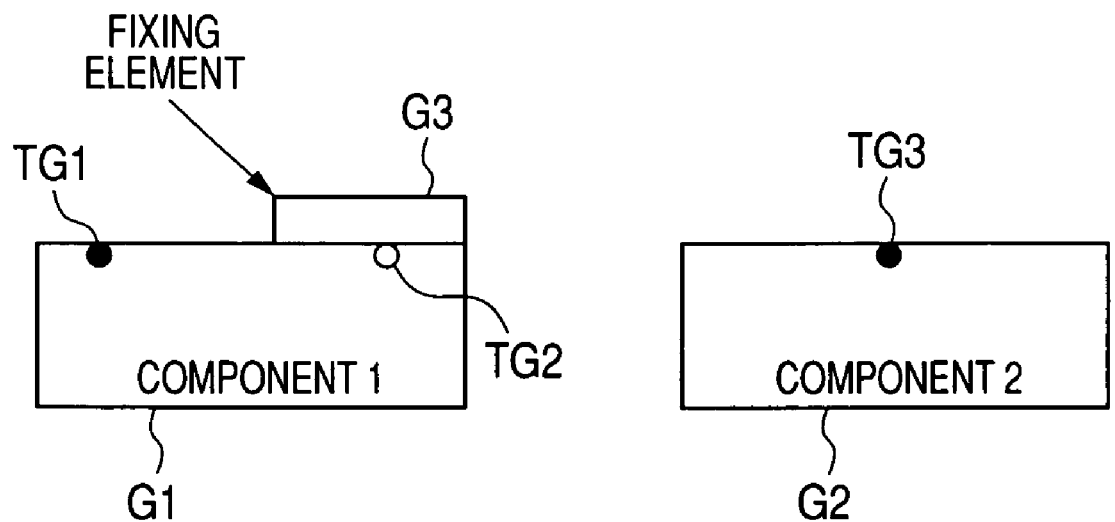
JOIN THE COMPONENTS AND SLIDE THE FIXING ELEMENT
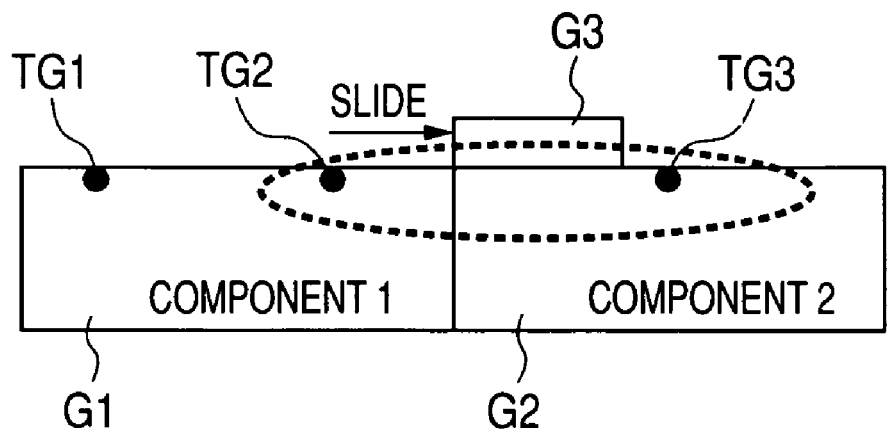
TAGS IN THIS AREA ARE READ TOGETHER
● IC TAG THAT CAN BE READ
○ IC TAG THAT CANNOT BE READ

ASSEMBLY WORK SUPPORTING METHOD AND SYSTEM

CLAIM OF PRIORITY

The present application claims priority from Japanese Patent Application 2007-331323 filed on Dec. 25, 2007, the content of which is hereby incorporated by reference into this application.

TECHNICAL FIELD

The present invention relates to a method and system for supporting assembly work including coupling components. In particular, the invention relates to a method and system that provide support for correct coupling of components in assembly work by using IC tags attached to individual components.

BACKGROUND OF THE INVENTION

Methods of making sure whether a device is set up properly are disclosed in, for example, Japanese Published Patent Application No. 2007-151383 (corresponding to US2007/0102505 A1), and Japanese Published Patent Application No. 2006-268079.

In a medical sector, conventionally, actions taken by medical staff have been made sure visually, which was insufficient to prevent medical malpractice such as use of an incorrect medical device and misidentification of patients. Recently, there is a major trend to prevent medical malpractice by introduction of IT (Information Technology) in clinical practice, making use of bar codes and IC tags. Methods of making sure whether the combination of a medical device, a drug, and a patient is correct are disclosed in, for example, Japanese Published Patent Application No. 2004-287616 (corresponding to US2004/0102505 A1), and Japanese Published Patent Application No. 2005-157936.

A collision avoidance method that is used in reading plural IC tags is disclosed in, for example, Japanese Patent No. 3565217 (corresponding to US2004/0085208 A1).

SUMMARY OF THE INVENTION

The method of Japanese Published Patent Application No. 2007-151383, US2007/0102505 A1, after connecting a cable to a terminal, serially reads IC tags individually attached to the cable and terminal, checks whether the ID of a terminal to which the cable should be connected matches the ID of the terminal which has been read, and detects whether the connection is correct. However, if plural IC tags attached to different terminals are read, this method cannot determines whether the connection is correct. Since IC tags are read one by one in order, reading takes more time than in the case of reading plural IC tags together. Because it is required to read IC tags one by one certainly, there is a high possibility of reading a wrong IC tag and retrying work is likely to occur.

In the method of Japanese Published Patent Application No. 2006-268079, IC tags are attached to joint parts of components and, in each IC tag, its ID and the ID of the mating component to be coupled are memorized. When components are coupled, their IC tags communicate with each other. Each IC tag determines whether the ID which has been read is correct ID (the component to be coupled). However, this method requires that, in the IC tag of each component, the ID of the IC tag attached to the mating component must be memorized beforehand. In case of design change, for example, use of a component having the same shape, but made of a different material, the memory on the IC tag of each component must be rewritten. Hence, this method is not adaptable to swift design change flexibly.

In the method of Japanese Published Patent Application No. 2004-287616, US2004/0102505 A1, when a patient, a drug, and a nurse respectively equipped with IC tags come sufficiently close to an IC tag reader installed near a bed, their IDs are acquired from the IC tags. From the acquired ID information, it is determined whether the patient, drug, and nurse are correct. In this method, these objects are determined to be "correct", if the IC tags to be present all exist within the reading region. However, this "correctness" depends on whether the patient, drug, nurse, device, etc. exist in a space where medical practice is performed, for example, near the bed. Therefore, the method cannot verify whether a medical apparatus is set up correctly, for example, whether the combination of a patient, an instillation apparatus, a drug for instillation is correct (whether the drug is set properly in the instillation apparatus).

The method of Japanese Published Patent Application No. 2005-157936 also determines whether IC tags attached to a patient, medical staff, and medical medium have been read within a given time period with an IC tag reader installed at the patient's bed or the like. However, in this method also, the objects are determined to be "correct", if the IC tags to be present all exist within the reading region, as is the case for Japanese Published Patent Application No. 2004-287616, US2004/0102505 A1. The method can verify the existence of the nurse, device, etc., but cannot verify whether a medical apparatus is set up correctly.

In these prior art techniques, reading each individual IC tag certainly is required. In the case that plural IC tags are read, it cannot be determined whether device setup or combination is correct and there is a high possibility of erroneous reading. Even if it is possible to determine whether components are coupled correctly, it is difficult to adapt to design change or the like flexibly. Even if it is possible to verify that a device and related parts required for assembly exist within a wide space, it is difficult to determine whether device setup or combination is correct.

The present invention is intended to provide a method and system for supporting assembly work, the method and system being capable of detecting whether components are combined and coupled correctly in assembly work by accurate and simple operations and adapting to design change such as component change flexibly.

A typical aspect of the invention disclosed herein is outlined below. A method for supporting assembly work of the present invention reads a first IC tag attached to a joint part of a first component and a second IC tag attached to a joint part of a second component together in a manner of preventing collision and determines whether the first component and the second component are coupled correctly, based on information representing mating relations of IC tags memorized beforehand.

According to the present invention, by reading IC tags attached to joint parts of components in assembly work, it can be detected accurately whether the components are combined and coupled correctly.

BRIEF DESCRIPTION OF THE DRAWINGS

FIG. 5B is an exemplary diagram illustrating several databases according to the second embodiment;

FIG. 11 is an exemplary diagram illustrating an IC tag that becomes readable after coupling according to a fourth embodiment; and FIG. 12 is an exemplary diagram illustrating an IC tag that becomes readable after coupling according to the fourth embodiment.

DETAILED DESCRIPTION OF THE PREFERRED EMBODIMENTS

An embodiment in which the present invention is implemented will be described below, using Figures. Particularly, in this embodiment, a process of assembling plural components into a device is characterized by, after coupling components, reading plural IC tags attached to the joint parts of the components together and determining whether the components are coupled correctly by a check against information representing mating relations of IC tags already registered in a work management server MNS. Here, reading the IC tags together means reading the IC tags of the components falling within a narrow area corresponding to a joint part between the components by one reading operation. The joint region is a narrow area including plural IC tags to be read, attached to the joint parts of the components. The number of IC tags to be read together is not restrictive and these tags may be plural IC tags attached to the joint parts of the components.

When IC tags are read together, a collision avoidance technique is used. The collision avoidance technique is generally a technique for identifying plural densely disposed IC tags. Conventionally, this technique is used for reading and identifying a large number of IC tags disposed in a wide area by an IC tag reader function with a long reading range as in a process of checking articles in physical distribution. On the other hand, in the present embodiment, the use of an IC tag reader function with a short reading range is assumed for reading only IC tags attached to the joint parts of components or the like. This technique is used to read plural IC tags attached to the joint parts together without fail. A reading range, e.g., from several millimeters to several centimeters may be set.

In the present embodiment, as IC tags attached to the joint parts of components, small IC tags, including an antenna, are used for a device or the like including small components, like an instillation device, but the size of IC tags depend on the size of components.

First Embodiment

The following description explains an example of application of the present invention to assembly work in which a worker assembles plural components into a device.

Figure 1:
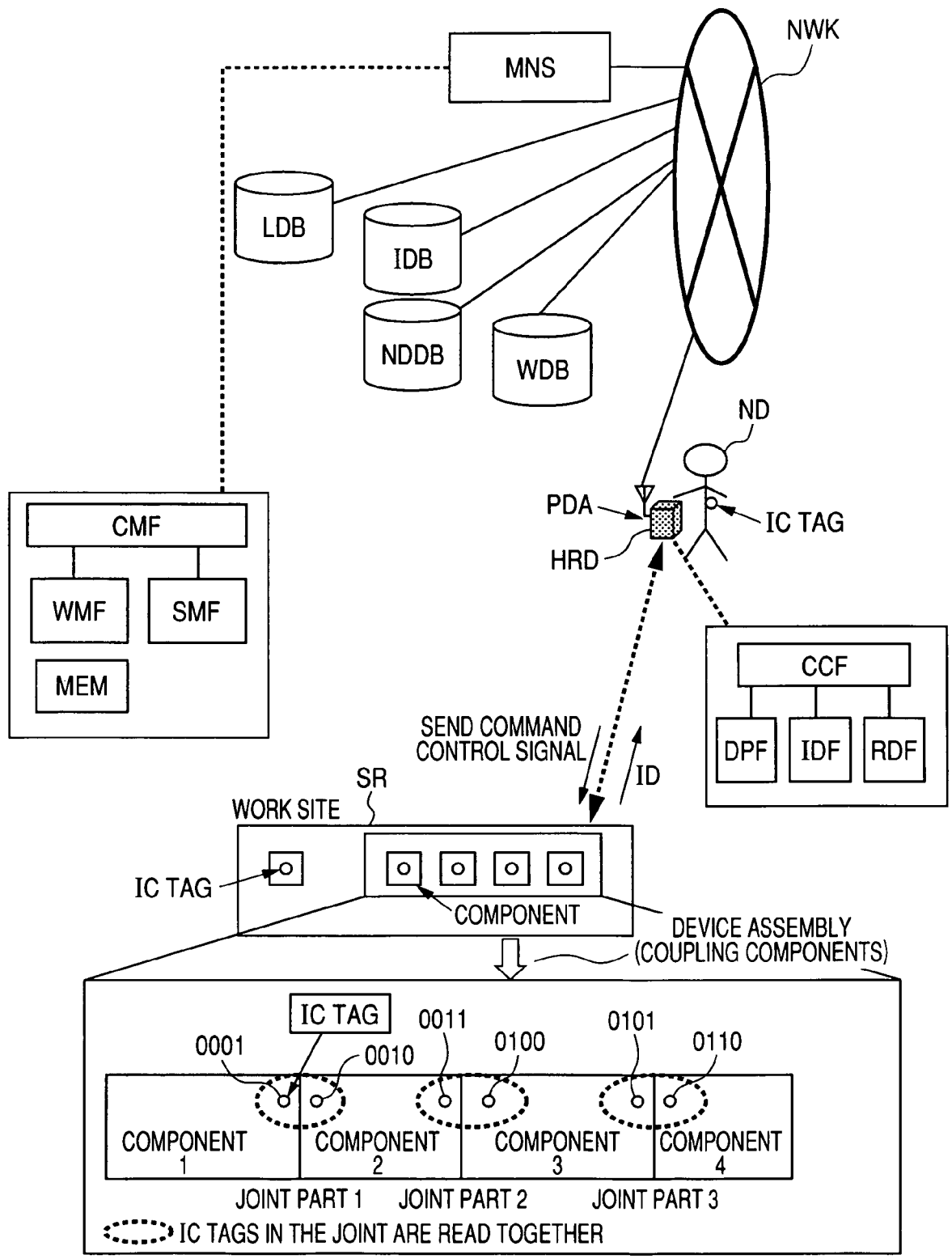
FIG. 1 is an exemplary diagram showing a system architecture according to a first embodiment.
Figure 2:
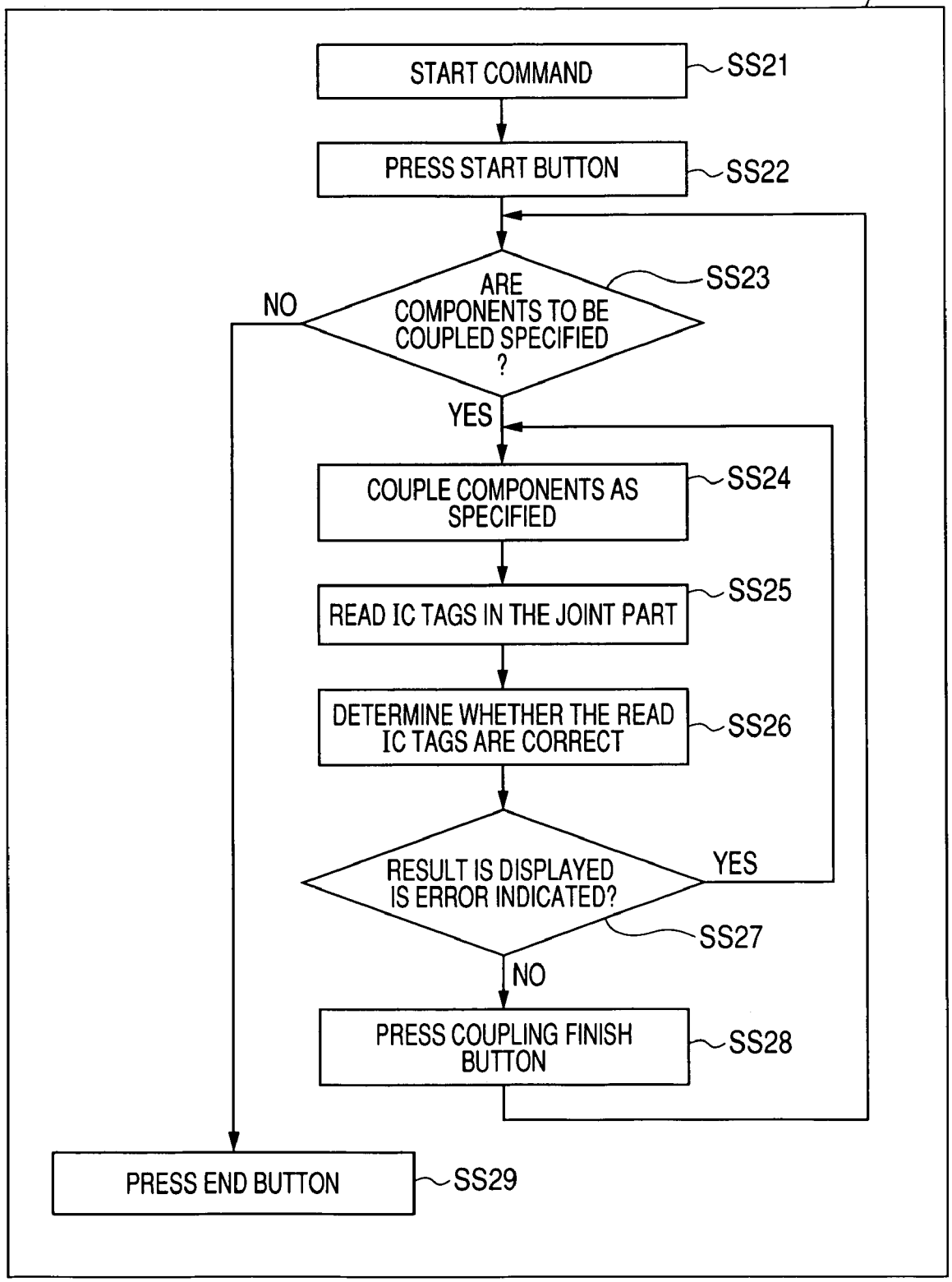
FIG. 2 is an exemplary flowchart illustrating a process flow according to the first embodiment.

FIG. 1 is a diagram showing a system architecture of a first embodiment. FIG. 2 is a process flowchart of the first embodiment.

Based on FIG. 1, an entire system architecture is described. A work management server MNS includes a system control unit CMF that determines whether a work is done correctly based on information stored in a memory MEM. The system control unit CMF registers and manages what should be done by a worker ND into a work process database WDB through a work process management unit WMF and registers and manages a work history into a history database LDB. Also, it registers and manages stocks of components, information representing mating relations between the joint parts of components and mating components to be coupled to the joint parts, and others into a component database IDB through a component management unit SMF. Further, it sends and receives various data to/from a mobile terminal HRD. In the memory MEM of the work management server, information representing mating relations of IDs (identification data) of IC tags attached to the joint parts. The work management server MNS may be a single server or its function may be distributed across plural servers; how it is implemented is not restrictive. If each of the above functions is distributed across separate servers, an effect of promoting more efficient process throughput in a large-scale factory or medical facility, etc. can be expected.

A device associated with a work, each of components of the device, a joint part of each component, and a worker are assigned specific IDs respectively, and IC tags having these specific IDs stored therein are installed. These specific IDs are stored in the component database IDB and the worker database NDDB appropriately. These databases are linked to the work management server MNS via a network NWK.

Further, each worker ND has a mobile terminal HRD, for example, PDA or PHS. The mobile terminal HRD includes an IC tag reading unit RDF having an IC tag reader function, a display and messaging unit DPF for displaying and messaging an instruction form the work management server MNS, a control communication unit CCF for communication with the work management server MNS via the network NWK, and an input unit IDF including buttons used for the worker ND to respond to an instruction from the work management server MNS. The IC tag reading unit RDF includes a collision avoidance function which will be described later.

Communication between the mobile terminal HRD and the work management server MNS may be accomplished wirelessly so that both can always communicate with each other or a wired connection to the network NWK may be established as required so that necessary information may be downloaded or uploaded; how it is implemented is not restrictive. In the present embodiment, an example is taken where a PDA that can always communicate with the server MNS is used as the mobile terminal HRD.

Then, referring to a process flow SFL shown in FIG. 2, a work outline is described in a case where a worker ND performs assembly work which plural components are assembled into a device. All steps of the process flow described below are performed by executing programmed instructions on the work management server or the mobile terminal. These programmed instructions are previously stored in the work management server or the mobile terminal, as in a general computer system, and its CPU (not shown) reads and executes these instructions.

First, a start command for a device assembly work is sent from the work management server MNS to the mobile terminal HRD that the worker ND has via the network NWK. The work start command is displayed on the display and messaging unit of the mobile terminal HRD (SS21). With the display of the command on the screen, an LED attached to the mobile terminal HRD may light or an audible alert such as a buzzer may be activated to alert the worker. This can ensure that the work start command is conveyed to the worker ND.

Knowing that the start command has been issued, the worker ND performs a work as specified. In the present embodiment, components to be coupled are assumed to be specified for each coupling step of the work. Thereby, after confirming whether coupling is done correctly for each coupling step, components to be coupled in the next step can be specified and the possibility of a coupling error can be reduced.

The worker ND presses the work start button on the mobile terminal HRD (SS22); when components to be coupled are specified (SS23), couples the components as specified (SS24); and performs reading of the IC tags attached to the components in the joint together by using the IC tag reader function of the mobile terminal HRD (SS25). When plural IC tags are read, the IC tag reading unit of the mobile terminal HRD performs collision avoidance processing. The reading result is sent to the work management server MNS. The system control unit CMF determines whether the components are coupled correctly (SS26) and sends the result to the mobile terminal HRD, and the result is displayed on the display unit (SS27).

If the coupling has been determined to be incorrect, an error is indicated on the display unit, based on which the worker ND retries the coupling (SS24). If the coupling has been determined to be correct, the worker ND presses the coupling finish button (SS28). This work is repeated until components to be coupled are no longer specified, then the worker ND presses the end button on the mobile terminal HRD (SS29) and coupling of components terminates.

In the above work, results of each reading of the IC tags, the time when the tags were read, button operations on the mobile terminal HRD, results on whether coupling is correct, etc. are all sent to the work management server MNS and stored into the history database LDB through the work process management unit WMF.

Further details on the coupling work flow (SS23 to SS28) are described referring to FIG. 1. The work to be done is making up a device by coupling components 1 to 4 shown in FIG. 1. These components are coupled in three joint parts 1 to 3. It is assumed that, in a joint part 1 between components 1 and 2, an IC tag with ID 0001 is attached to the component 1 and an IC tag with ID 0010 to the component 2. It is assumed that, in a joint part 2 between components 2 and 3, an IC tag with ID 0011 is attached to the component 2 and an IC tag with ID 0100 to the component 3; in a joint part 3 between components 3 and 4, an IC tag with ID 0101 is attached to the component 3 and an IC tag with ID 0110 to the component 4.

It is assumed that coupling the components 1 and 2 is specified to the worker ND from the work management server MNS (SS23). The worker ND couples the components 1 and 2 (SS24) and executes reading the IC tags in the joint part 1 (SS25) together. That is, ID0001 and ID0010 are read by one reading operation.

Here, collision avoidance processing is performed to read plural tags together without fail. An explanation is provided about the collision avoidance processing in the present embodiment. First, first two bits of ID are specified as a time slot by the IC tag reading unit. This means making the IC tags respond to a read request from the IC tag reading unit with latency for each time slot value. This latency interval is predetermined for each time slot value and memorized in every IC tag. The IC tag reading unit sends an ID read request to the IC tags falling within a reading area. In this example, the IDs of the IC tags within the reading area are 0001 and 0010 and a value of "00" is read from each tag in this time slot. As a result, both send their ID subsets at the same time and collision occurs.

So, the IC tag reading unit shifts the time slot to following two bits (the last two bits of ID) and sends an ID read request to the IC tags falling within the reading area. In the present embodiment, because there are two IC tags having a value of "01" and a value of "10" which should be read in this time slot, one IC tag with ID0001 will send an ID subset of "01" in this time slot and the other IC tag with ID0010 will send an ID subset of "10" in this time slot. Then, the IC tag reading unit requests an IC tag within the reading area not to send an ID subset for a given interval, specifying the ID subset which has been read. Thereby, the IDs of the two IC tags are read in separate time slots. A total number of bits to be read in the time slots to be specified is predetermined. It is determined that the IDs of all IC tags have been read, as a total of four bits have read in the specified time slots.

After that, the IDs of the two IC tags, 0001, 0010 which have been read are sent to the work management server MNS. The system control unit CMF determines whether the coupling in the joint part 1 is done correctly by referring to information representing mating relations of IC tags stored in the memory MEM (SS26) and sends back the result to the mobile terminal. If it has been determined that the coupling is done correctly, information that the coupling is correct is displayed on the display and messaging unit of the mobile terminal HRD (SS27). Then, the worker ND presses the coupling finish button (SS28).

Next, an instruction to couple components 2 and 3 is displayed on the display and messaging unit of the mobile terminal HRD. The worker ND continues to perform the same work as described above until the coupling work terminates.

By using the collision avoidance technique in this way, it becomes possible to read plural IC tags attached to joint parts together without fail. By repeating the work of reading plural IC tags together, it is possible to detect whether the components are properly coupled with accuracy and by simple operation. Since instructions for work and results on whether coupling is correct, etc. are provided and displayed on the mobile terminal that the worker has, an error in the work can be prevented.

Although the above flow described a method in which the work steps are sequentially performed with communication being carried out between the mobile terminal and the work management server, the mobile terminal may receive and memorize information representing the mating relations of IC tags from the work management server beforehand, the control communication unit may determine whether coupling is correct and send the result to the work management server. Thereby, there is no need for the mobile terminal and the work management server to always communicate with each other. This decreases the processing load of the work management server and can lighten the communication load.

In reading plural IC tags falling within a narrow region together and determining whether components or the like are coupled correctly, an IC tag other than target IC tags to be read may be read. For this case, an explanation is provided below about how to determine whether coupling is correct. The target IC tags to be read denote IC tags whose IDs matching the mating relations stored in the work management server or the mobile terminal.

In the present embodiment, a threshold value in the number of IC tags allowed to be read other than the IC tags to be read or a threshold value in the number of IC tags allowed to be read together is predetermined. The system control unit determines that coupling of components or the like is correct, if the number of IC tags that have been read does not exceed the threshold value and if all IC tags to be read are included. It determines that coupling of components or the like is incorrect, if the number of IC tags that have been read exceeds the threshold value or if the IC tags to be read are not included.

Figure 9:
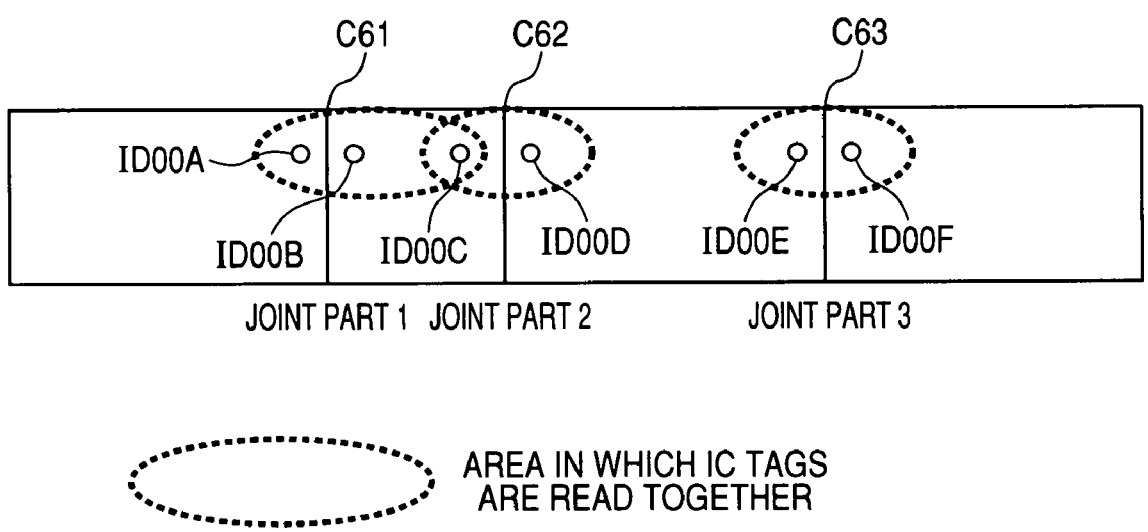
FIG. 9 is an exemplary diagram explaining a method of determining whether coupling is done correctly according to the first embodiment.

A particular explanation is provided referring to FIG. 9. In FIG. 9, there are three joint parts and it is assumed that combinations of target IC tags to be read are "ID00A, ID00B" in a joint part 1 (C61), "ID00C, ID00D" in a joint part 2 (C62), and "ID00E, ID00F" in a joint part 3 (C63). A threshold value in the number of IC tags allowed to be read other than those to be read is assumed to be 1.

It is assumed that the IC tags that have been read in each joint part by the worker have the following IDs: "ID00A, ID00B, ID00C" in the joint part 1; "ID00C, ID00D" in the joint part 2; and "ID00E, ID00F" in the joint part 3. In this case, all IDs of the IC tags to be read are included in those that have been read in each joint part. In reading in the joint part 1, the number of IC tags read other than those to be read is 1 and, therefore, all couplings are determined to be correct.

The threshold value in the total number of IC tags allowed to be read other than those to be read or in the total number of IC tags allowed to be read together may be set for each assemble work. In the foregoing case, if a threshold value of 0 is set with regard to the total number of IC tags allowed to be read other than those to be read, since the total number of IC tags read other than those to be read in the joint parts 1 to 3 is 1, the assembly work is determined to be incorrect. In this case, the worker retries the assembly work and the assembly work will be determined to be correct upon reading of only the IC tags to be read.

In this way, by setting a threshold value in the number of IC tags to be read in each joint part or a threshold value in the number of IC tags to be read throughout the assembly work, the probability of error reading of IC tags can be reduced and it can be detected more accurately whether components or the like are coupled correctly (the assembly work is done correctly).

Second Embodiment

In a second embodiment, a description is provided for an example of application of the present invention to assembly work of an instillation device which is performed in a medical sector.

Figure 3:
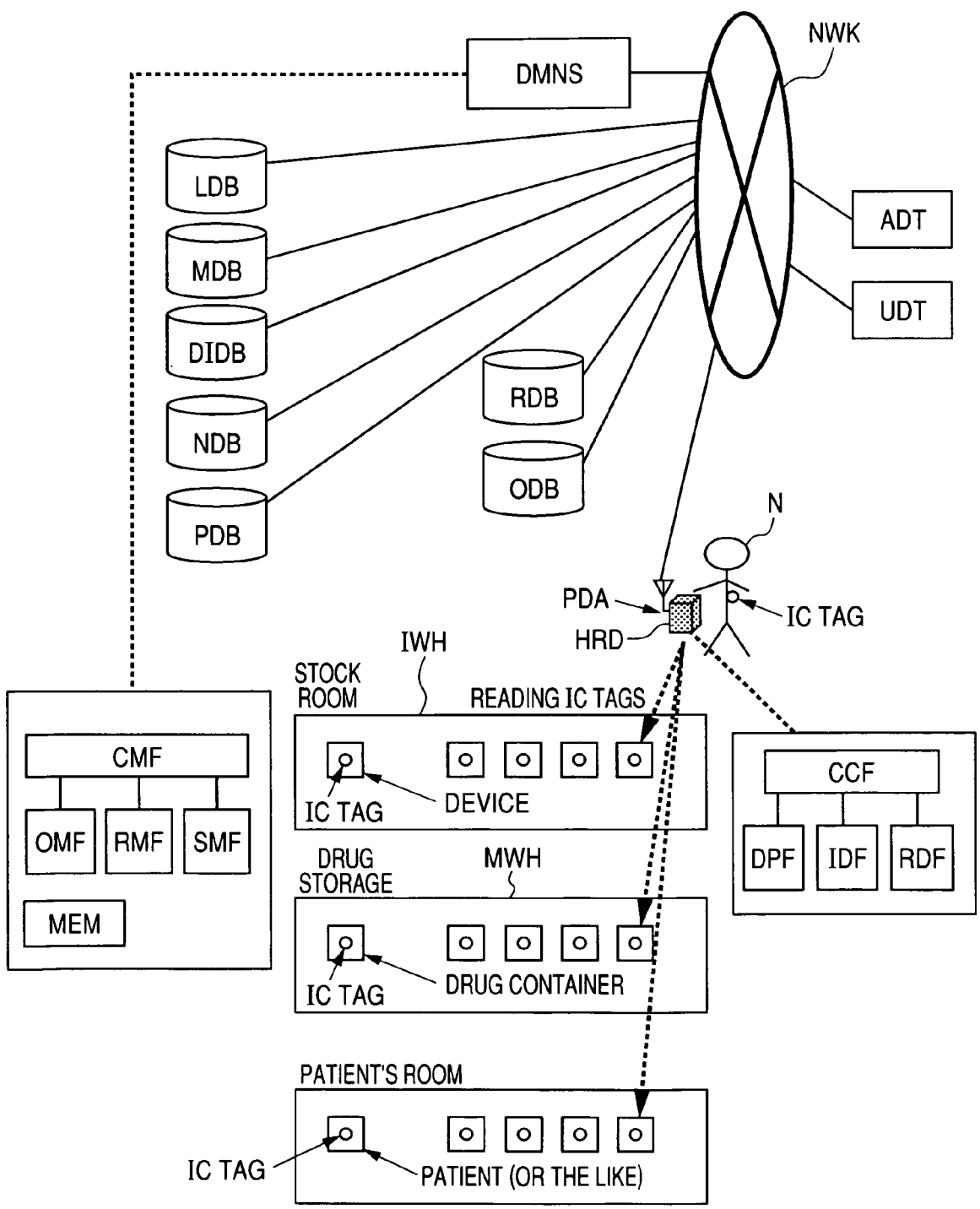
FIG. 3 is an exemplary diagram showing a system architecture according to a second embodiment.

To begin with, a system architecture of the second embodiment is described based on FIG. 3. Entities corresponding to those in the system architecture of FIG. 1 are assigned the same symbols and duplicate descriptions already provided in the first embodiment are omitted. A system control unit CMF of a medical management server DMNS registers and manages medical instructions to medial staff N in an order database ODB through an order management unit OMF and registers and manages medical records created by a doctor into a medical record database RDB through an electronic medical record unit RMF. It also registers and manages stocks of drugs and medical devices, information representing mating relations between the joint parts of components of a device and mating components to be coupled to the joint parts, and others into a medical device database DIDB and a drug database MDB through a component management unit SMF. Further, it registers and manages information about medical staff and patients into a medical staff database NDB and a patient database PDB.

Moreover, a user terminal UDT that is used by medical staff such as doctors and nurses and an administrative terminal ADT for an information administrator are connected to the medical management server DMNS and the databases via a network NWK.

Figure 5A:
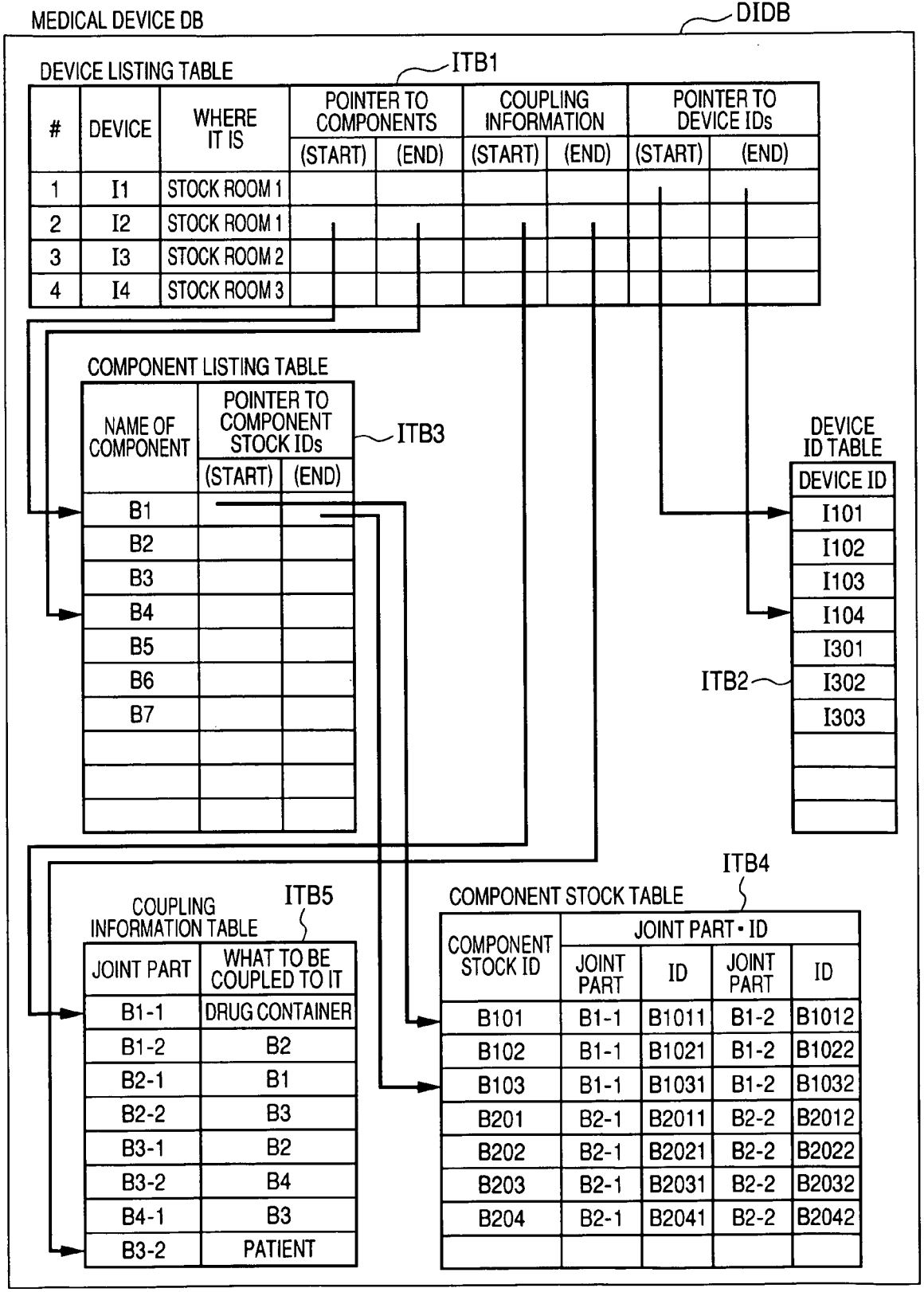
FIG. 5A is an exemplary diagram illustrating a medical device database according to the second embodiment.

The contents of the databases are illustrated in FIGS. 5A and 5B. Data are registered in advance into these databases and managed before a doctor issues an order.

The medical device database DIDB is a database in which types and components of devices which are used for medical care and treatment and stocks of the devices and components are stored. This database includes the following tables: a device listing table ITB1 in which names of devices are stored; a device ID table ITB2 in which IDs of device stocks are stored, if a device includes a single component or if a device does not have to be assembled in a place where it is used; a component listing table ITB3 in which names of components are stored, if a device includes plural components; a component stock table ITB4 in which IDs of component stocks and joint parts of components and their IDs are stored; and a coupling information table ITB5 in which mating relations between joint parts of a device and mating components to be coupled to the joint parts are stored.

The tables ITB1 to ITB5 are related to another table among them by pointers. For example, the name of a device I1 registered in the device listing table ITB1 is a device that does not have to be assembled and has a pointer to the device ID table ITB2. The pointer points a range of device IDs I101 to I104 in the device ID table ITB2, that is, it indicates that the device I1 has four stocks with IDs I101 to I104.

The name of a device I2 registered in the device listing table ITB1 is a device including plural components and has a pointer to the component listing table ITB3 and a pointer to the coupling information table ITB5. The pointer to the component listing table ITB3 points the names of components B1 to B4 and it indicates that the component I2 includes these four components. A pointer from the component B1 extends to the component stock table ITB4 and indicates a range of component IDs of B101 to B103. It indicates that the component B1 has three socks with IDs of B101 to B103. Further, a component with the component ID of B101 has a joint part B1-1 and a joint part B1-2, which indicates that IC tags with IDs of B1011 and B1023 are attached to the joint parts respectively. To other components as well, IC tags with IDs that are non-duplicative are attached.

Meanwhile, because the device I2 includes four components, eight IC tags exist on it, if one IC tag is attached to each joint part of each component. Hence, the pointer to the coupling information table ITB5 from the name of the device I2 in the device listing table ITB1 points the names of eight joint parts. It is denoted that a drug is coupled to a joint part B1-1, i.e., one joint part of the component B1 and a component B2 is coupled a joint part B1-2, i.e., the other joint part of the component B1. The drug does not have a component name like the component B2. Likewise, it is denoted that the component is coupled to a joint part B2-1, i.e., one joint part of the component B2 and a component B3 is coupled to the other joint part of the component B2, and so on.

The drug database MDB is a database in which drugs for use in medical treatment and stocks thereof are stored. The names of drugs and, for each drug, place of storage, quantity, relevant IDs (the IDs of stocks of the same drug, if exist) are stored.

The medical staff database NDB is a database in which information about medical staff is stored. For each staff, name, function, department, and ID are stored.

The patient database PDB is a database in which patient information is stored. For each patient, name, ID, medical record ID, patient's room, room ID, bed, and bed ID are stored.

The medical record database RDB is a database in which information for medical records is stored. For each medical record, ID and a pointer to medical record content are stored. Herein, detailed description of medical record content is omitted. Since a medical record ID is associated with an order ID which will be described below, the medical management server can manage what treatment has been done for an order issued by a doctor.

The order database ODB is a database in which orders are stored. For each order, ID, associated medical record ID, and a pointer to order content are stored. Order content which is, for example, illustrated in FIG. 6 is stored.

Figure 6:
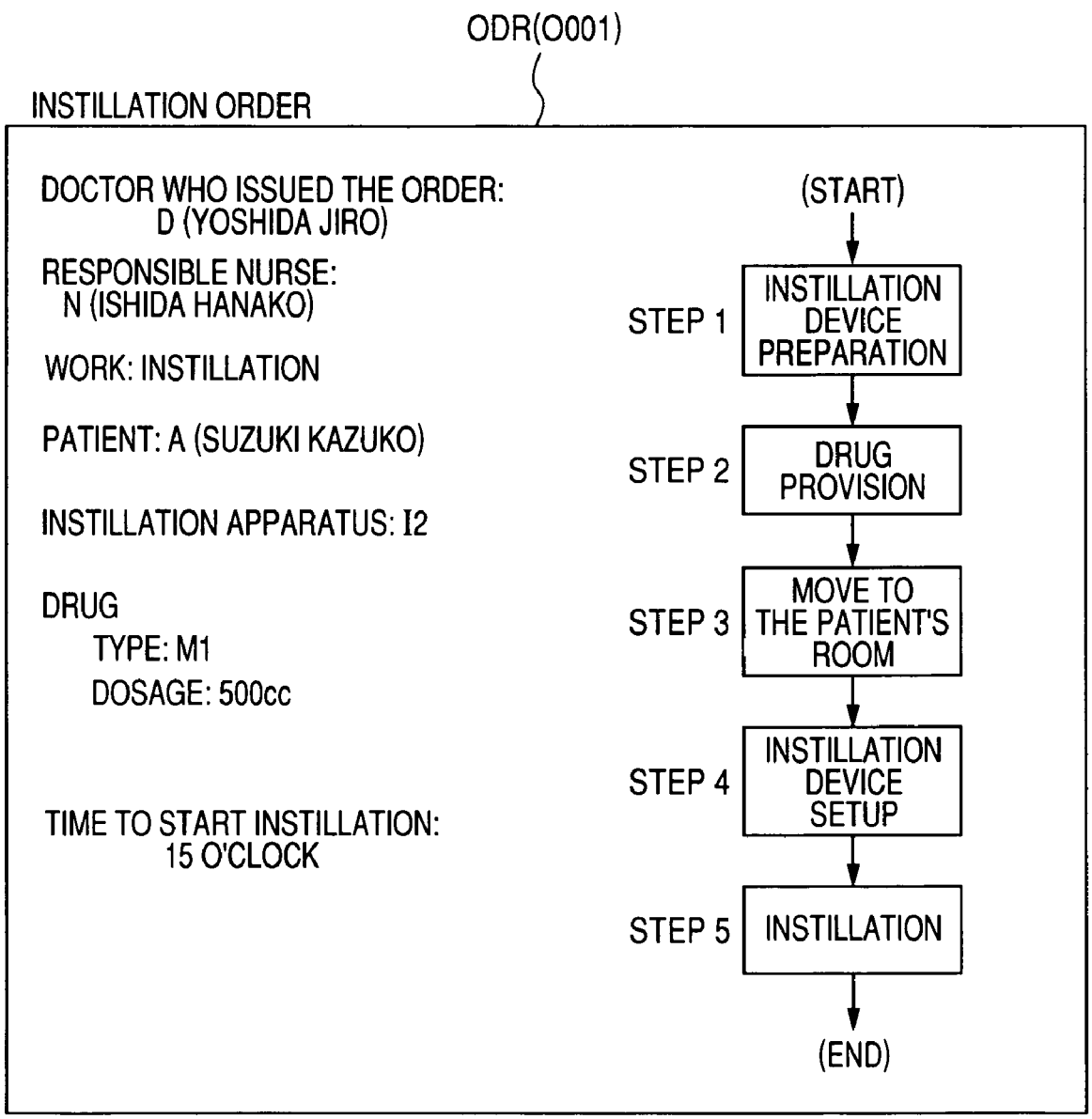
FIG. 6 is an exemplary diagram illustrating an instillation order according to the second embodiment.
Figure 7A:
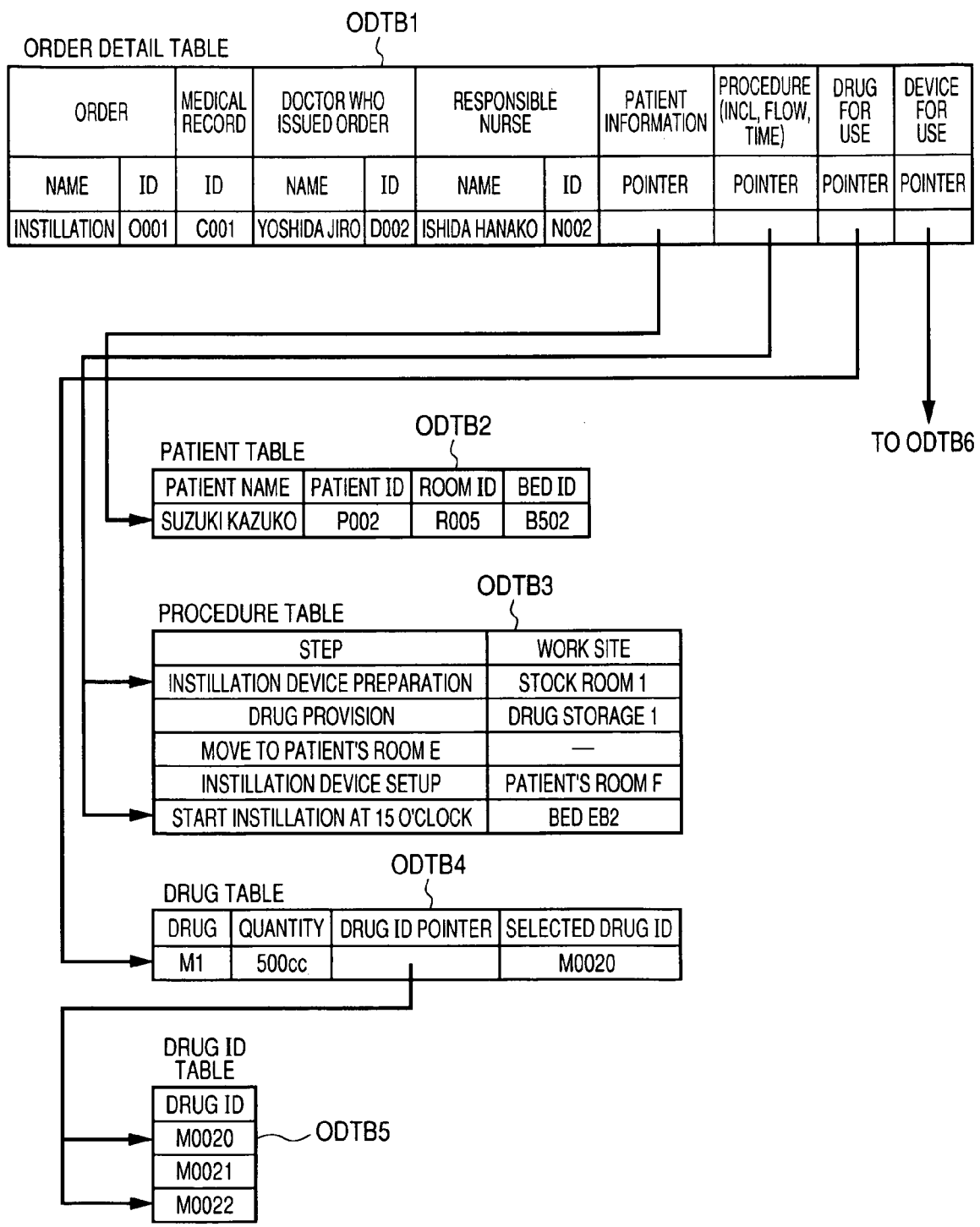
FIG. 7A is an exemplary diagram illustrating a set of order tables according to the second embodiment.
Figure 7B:
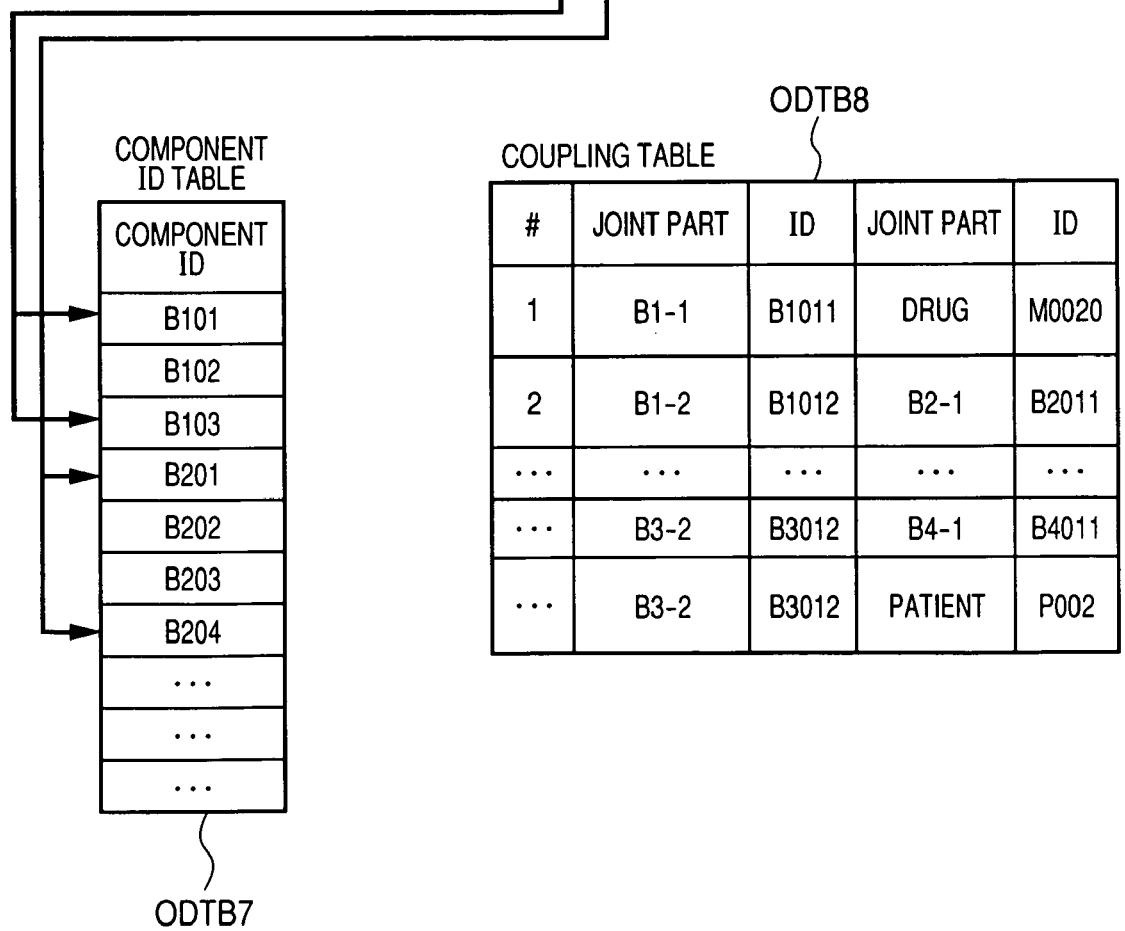
FIG. 7B is an exemplary diagram illustrating a set of order tables according to the second embodiment.

When a doctor issues a distillation order (ODR) which is illustrated in FIG. 6 through a user terminal, the medical management server creates a set of order tables ODTBs, referring to the databases. These tables are explained below referring to FIGS. 7A and 7B. These order tables are used to detect whether each step of the order is performed correctly by a medical staff N. These tables are created by the medical management server and stored in the memory MEM of the medical management server. The medical management server creates the order tables for each order by referring to the databases and updates the tables, so that the contents of the tables are adaptive to an order change or the like flexibly.

An order detail table ODTB1 is created based on the medical staff database NDB. This table includes the name of the order, order ID, medical record ID, the name and ID of the doctor who issued the order, the name and ID of the responsible nurse, a pointer to a patient table ODTB 2 in which patient information is stored, a pointer to a table ODTB3 in which procedural steps are stored, a pointer to a drug table ODTB 4 in which information on the drug for use is stored, and a pointer to a device for use table ODTB 6 in which information on the device for use is stored.

The patient table ODTB2 is created based on the patient database. This table includes the patient name, patient ID, room ID, and bed ID.

The procedure table ODTB3 is created based on the medical device database DIDB, the drug database MDB, and the patient database PDB. This table includes a series of procedural steps and relevant work sites.

The drug table ODTB4 is created based on the drug database MDB. This table includes the drug name, quantity, a pointer to a drug ID table ODTB 5 in which a list of IDs of drug stocks is stored, and the selected drug ID. In the selected drug ID field, the drug ID selected by the nurse in step 2 (drug provision) is stored.

The device for use table ODTB 6 for storing information about the device for use is created based on the medical device database DIDB, the medical staff database NDB, and the patient database PDB. This table includes the name of the device for use, a pointer to a component ID table ODTB7 in which a list of the IDs of the stocks of the components of the device is stored, other information (drug, patient, nurse), and selected IDs. In the fields of selected IDs for B1 to B4 and M1, the IDs of the components and the ID of the drug selected by the nurse in step 1 (instillation device preparation) and step 2 (drug provision) are stored.

Figure 4:
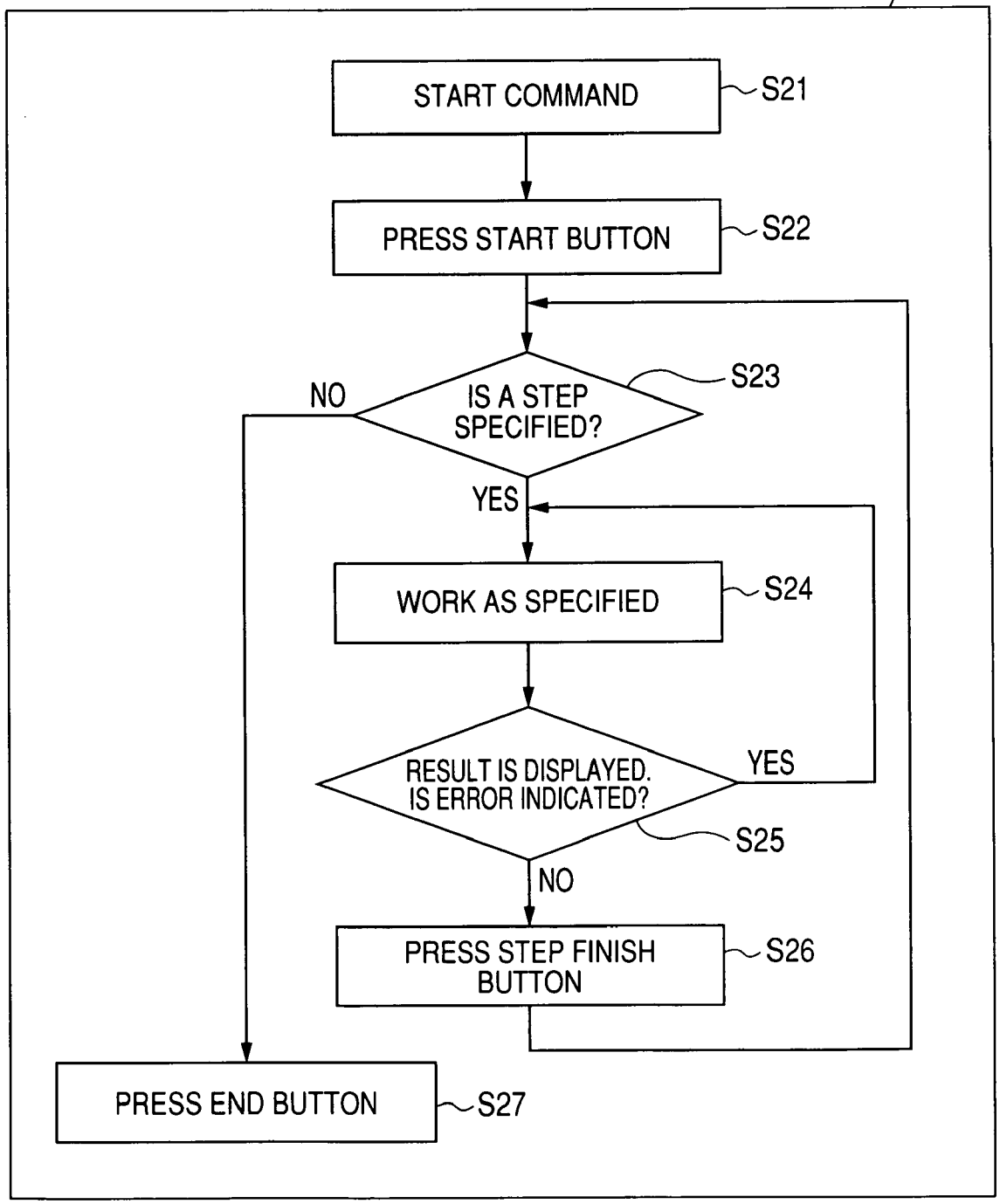
FIG. 4 is an exemplary flowchart illustrating a work flow according to the second embodiment.
Figure 8:
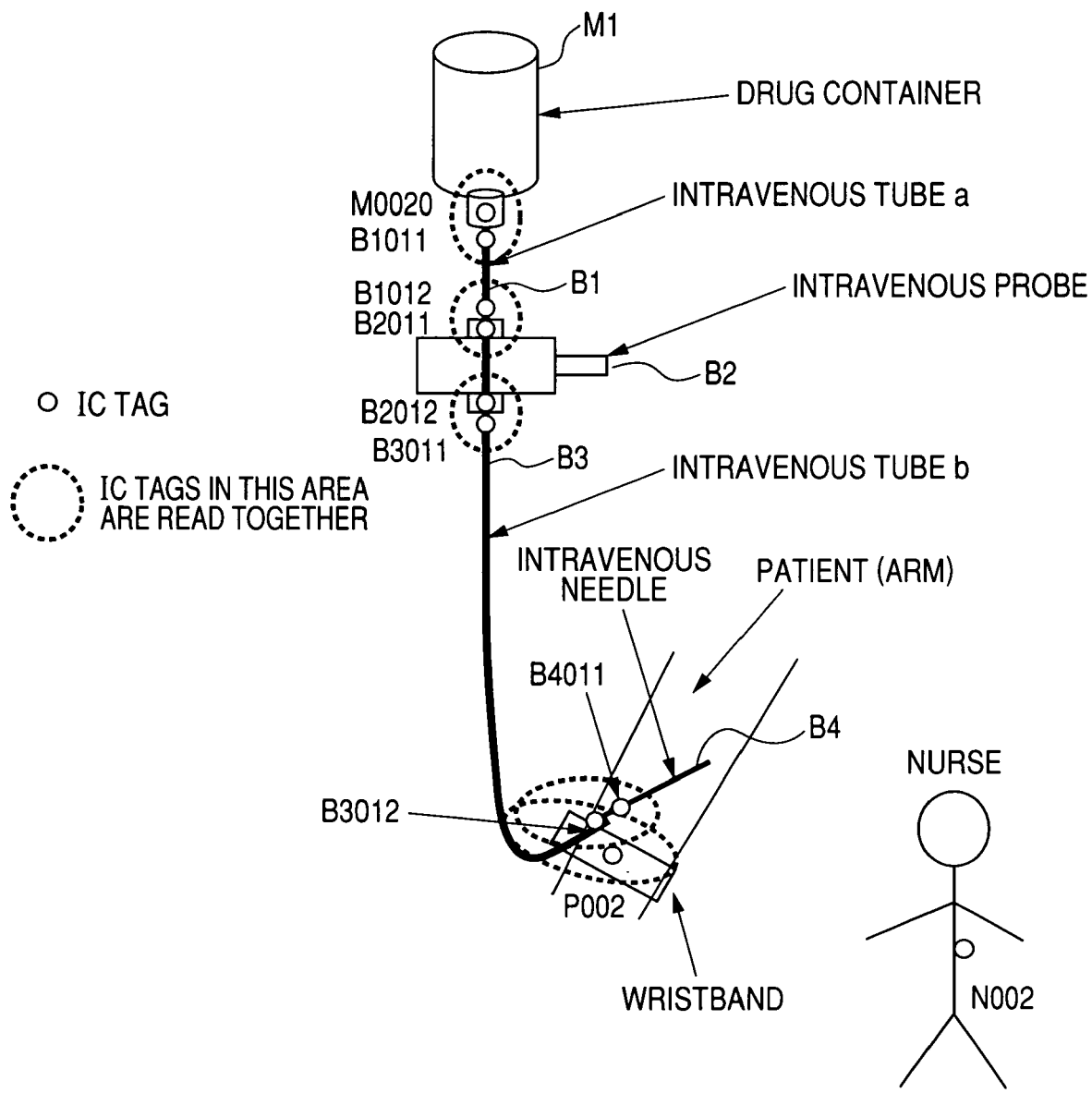
FIG. 8 is an exemplary diagram illustrating the assembly of an instillation apparatus according to the second embodiment.

The coupling table ODTB8 is created based on the medical device database DIDB to indicate the mating relations of the joint parts (IDs) of the components and the IC tag (ID) attached to the patient. Based on the components and drug or the like selected by the medical staff, all joint parts and IDs are stored so that a joint part (ID) is mapped to its mating joint part (ID) to be coupled. Then, for the case that the instillation order shown in FIG. 6 has been issued, the flow of the work that should be done by a nurse N is explained referring to FIG. 4 illustrating procedural steps of the work and FIG. 8 showing the schematic of the apparatus.

The issued order is sent from the system control unit to the mobile terminal that the nurse has. The display and messaging unit of the mobile terminal shows that the order has been issued and the work start command is displayed (S21). In the present embodiment, work instructions are given for each step. The nurse presses the work start button on the mobile terminal (S22) and the result is sent to the medical management server.

In step 1, referring to the procedure table ODTB3, the medical management server specifies the step 1 (S23) as follows: it sends an instruction to get the components of the instillation apparatus 12 and information that the components of the instillation apparatus 12 are an intravenous tube a (B1), intravenous probe (B2), intravenous tube b (B3), and intravenous needle (B4) to the mobile terminal.

Based on the component information displayed on the mobile terminal, the nurse selects the components of the instillation apparatus 12 at a stock room IWH. First, it is assumed that, from among three available stocks B101, B102, B103 of intravenous tubes a (B1), the nurse has selected B101 (S24). Each time a component is selected, the nurse performs reading of an IC tag attached to the component with the IC tag reader function.

The medical management server compares the result of the reading to IDs B101 to B103 of intravenous tubes a (B1) stored in the component ID table ODTB7 created. The result of the reading B101 is determined to be correct, as it is included in the above three IDs. This result is sent to the mobile terminal and displayed on the display and messaging unit of the mobile terminal. If an intravenous tube other than B101 to B103 has been selected, the medical management server determines that the selection is incorrect. In that case, on the display and messaging unit of the mobile terminal, an error is displayed (S25), based on which the nurse N retries component selection (S24). In this way, component selection is repeated for all the above-mentioned components. Here, it is assumed that the IDs of selected components are B101 of intravenous tube a (B1), B201 of intravenous probe (B2), B301 of intravenous tube b (B3), and B401 of intravenous needle (B4). Once all components have been selected correctly, a message of that is displayed on the mobile terminal, then the nurse presses the step finish button (S26).

In step 2, the system control unit specifies the provision a drug M1 to the mobile terminal (S23). The nurse performs reading of an IC tag attached to the drug container selected at a drug storage MWH (S24). Referring to the drug table ODTB3, the medical management server determines whether the result of the reading is correct and its result is displayed on the mobile terminal (S25). If the nurse has selected a container of 500 cc of drug M1, that is, if ID of M0020 or M0021 has been read, it is determined to be correct. When this result (the selected drug container is correct) is displayed on the mobile terminal, the nurse presses the step finish button (S26). Here, it is assumed that the drug container with ID of M0020 has been selected.

The component IDs and drug ID selected by the nurse in the steps 1 and 2, as described above, are stored into the relevant fields of selected ID in the device for use table and the joint parts of the components and their IDs are stored into the coupling table.

In step 3, the medical management server specifies moving to a patient's room E to the mobile terminal (S23). The nurse N performs reading of an IC tag installed at the entrance of the patient's room E, an IC tag attached to the patient A, and an IC tag attached to the nurse's name tag (S24). Referring to the order detail table ODTB1 and the patient table ODTB2, the medical management server determines whether the result of the reading is correct and its result is displayed on the mobile terminal (S25). If IDs, R004, P002, N002 have been read, the reading is determined to be correct. When this result is displayed on the mobile terminal, the nurse presses the step finish button (S26).

In step 4, the work of assembling the components of the instillation apparatus is specified to the mobile terminal (S23). The assembly work includes coupling the intravenous tube a, intravenous probe, intravenous tube b, and intravenous needle in order. If the components with IDs of B101, B201, B301, B401 and the drug container with ID of M0020 have been selected, the IDs of IC tags being in their joint parts are as shown in FIG. 8. That is, in the joint part between the drug container and the intravenous tube, an "M0020" IC tag is on the drug container and a "B1011" IC tag on the intravenous tube a. In the joint part between the intravenous tube a and the intravenous probe, a "B1012" IC tag is on the intravenous tube a and a "B2011" IC tag on the intravenous probe. In the joint part between the intravenous probe and the intravenous tube b, a "B2012" IC tag is on the intravenous probe and a "B3011" IC tag on the intravenous tube b. In the joint part between the intravenous tube b and the intravenous needle, a "B3012" IC tag is on the intravenous tube b and a "B4011" IC tag on the intravenous needle.

First, the nurse couples the intravenous tube a and the intravenous probe and performs reading of the IC tags in the joint part therebetween. Here, plural IC tags exiting in the joint part is read together, using the collision avoidance technique as already stated (S24). For the IDs which have been read, the medical management server determines whether the coupling is done correctly, referring to the coupling table ODTB8, and its result is sent to the mobile terminal. If the IDs which have been read are B1012 and B2011, a message that the coupling is done correctly is sent to the mobile terminal and displayed; if not, a message that the coupling is incorrect is sent and displayed (S25). Likewise, the nurse couples the intravenous probe and the intravenous tube b, the intravenous tube b and the intravenous needle, and the drug container and the intravenous tube a in order. For each coupling, reading the IC tags together is performed and, after determining whether the coupling is done correctly, the result is sent and displayed.

After making sure that all components are coupled correctly, the nurse couples the intravenous tube b and the wristband of the patient and performs reading of the IC tags attached to the intravenous tube b and the wristband of the patient 1 together. Referring to the coupling table, if the IDs which have been read are B3012 and P002, the medical management server determines that combination of the component and the patient is correct. When this result is displayed on the mobile terminal, the nurse presses the step finish button (S26).

In this way, by repeating the operation of reading the IC tags together in each joint part, attached to the joint parts of the components of the instillation apparatus, the joint part of the drug container, and the patient, determining whether the components, drug, and patient are combined correctly can be carried out accurately and easily. Also, since work instructions and the result of determining whether the work is done correctly are displayed on the mobile terminal that the nurse has, it is possible to prevent medical malpractice. By putting the name tag of the nurse close to the wristband of the patient, reading of the IC tags of both may be performed. IC tags to be read together are not limited to IC tag combinations stored in the coupling table. The order in which the components are coupled is not limited to that described above.

In the above description, for each coupling, whether it is done correctly is determined; alternatively, on the completion of coupling all components, the medical management server may determine whether every coupling is correct. Considering a routine operation by a skilled nurse, after the assembly of the instillation apparatus, by performing at once the operation of determining whether every coupling is correct, shortening the operating time can be effected.

In step 5, an instruction to start the instillation at 15 o'clock is issued from the medical management server to the mobile terminal (S23). The nurse opens the intravenous probe and starts the instillation (S24), then presses the step finish button on the mobile terminal (S26). The medical management server checks the time when the step finis button was pressed and has the termination of the order displayed on the mobile terminal, then the nurse presses the end button (S27). This is the end of a series of operations based on the order.

Although, in the described embodiment, the order specifies the operation start time only for the step 5, start time may be specified for other steps and operation end time may be specified. Thereby, the responsible nurse can schedule the operating time and carry out operations smoothly.

Results of reading of all IC tags, the time when the tags were read, button operations on the mobile terminal, results on whether coupling is correct, etc. are stored in the history database LDB. Because all operation logs are stored in the history database, they can not only be used as a part of work logs, also can be used for work analysis on error-prone steps, the level of proficiency of each of nurses, etc.

Third Embodiment

Figure 10:
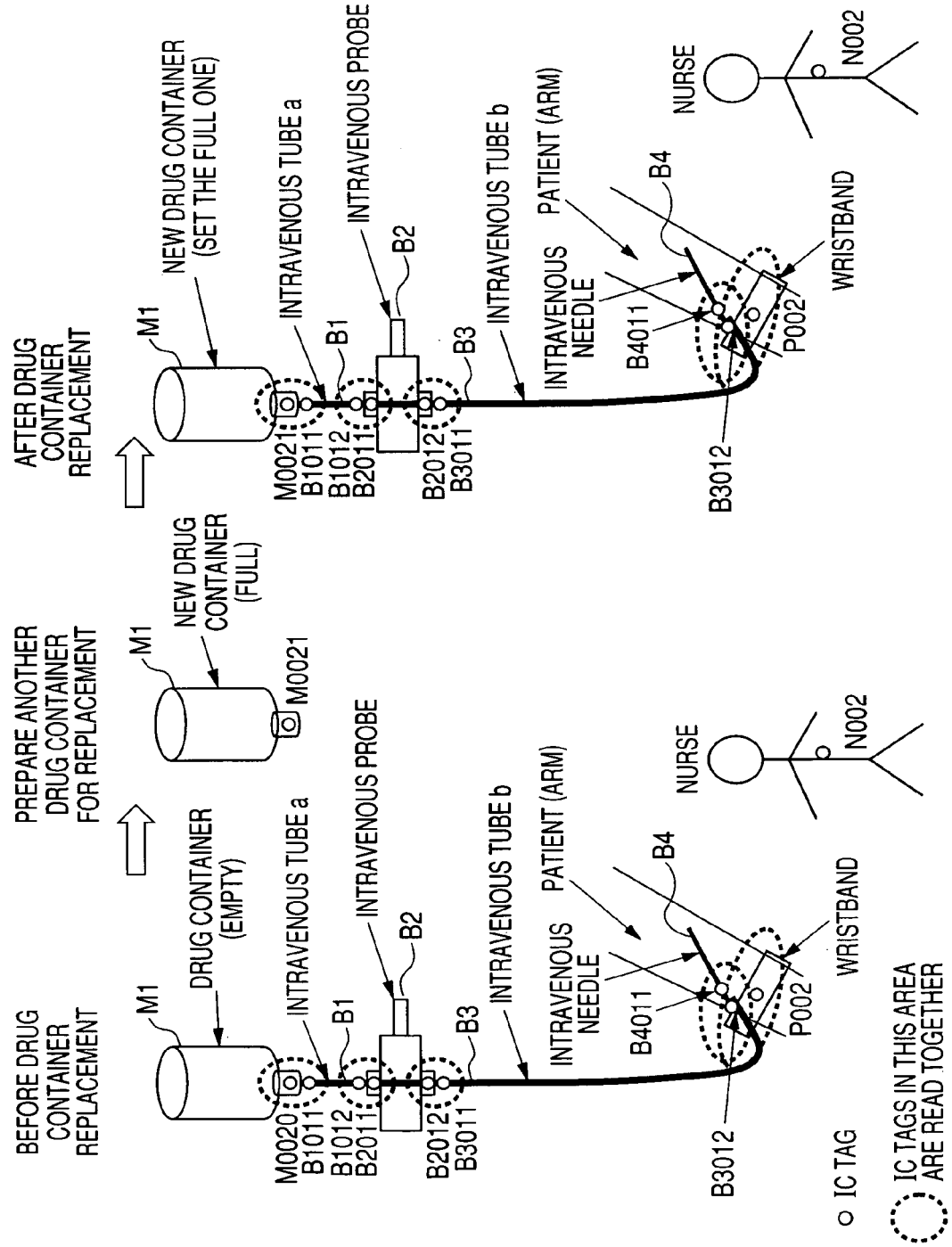
FIG. 10 is an exemplary diagram illustrating drug container replacement according to a third embodiment.

In a third embodiment, when instillation is performed, a method of drug container replacement is described referring to FIG. 10. Drug container replacement discussed herein should be performed in a case that the drug container has become empty and instillation is continued for the same patient or it is replaced with a container of another drug. However, this replacement does not include the replacement or change of the instillation apparatus. Duplicate descriptions on communication with the medical management server, button operations by a nurse, etc., already provided in the second embodiment, are omitted.

It is assumed that the doctor order specifies that, after the termination of instillation started from 15 o'clock, the instillation of 500 cc of drug M1 500 cc shall be continued using the instillation apparatus I2. The issued order is sent to the mobile terminal that the nurse has. The work that should be done by the nurse includes the following steps (1) to (5):

(1) Get a container of 500 cc of drug M1 from the drug storage MWH.

(2) Make sure that instillation of drug M1 by the instillation apparatus I2 has finished and close the intravenous probe.

(3) Remove the container of drug M1.
(4) Set a new container of drug M1.
(5) Open the intravenous probe and resume the instillation.

In step (1), the nurse gets a container of 500 cc of drug M1 from the drug storage MWH and performs IC tag reading. The same drug and quantity as in the second embodiment are used, but the new container is assigned a different ID (M0021 or M0022) from the ID (M0020) of the currently used drug M1. When the IC tag with ID of M0021 or M0022 is read by the nurse, the medical management server can identify the same drug M1 contained in a different container from the currently used drug M1 by referring to the device for use table and the component ID table (Prepare Another Drug Container for Replacement in FIG. 10). Herein, it is assumed that the container of drug M1 with ID of M0021 has been selected. In this case, information related to the drug M1 stored in the device for use table, the coupling table, etc. is updated.

In step (2), upon the end of the ongoing instillation, the nurse closes the intravenous probe and presses the step finish button.

In step (3), the nurse removes the container of drug M1 and performs reading of the IC tag (M0020) attached to the container. The medical management server can identify the container of the drug that was being instilled until now by referring to the history database.

In step (4), the nurse couples the new drug M1 container (M0021) to the intravenous tube 1 to set it in the instillation apparatus B. At this time, two IC tags in the joint part between the drug container and the intravenous tube are read together using the collision avoidance function (After Drug Container Replacement at right in FIG. 10). The medical management server judges the result of reading by referring to the updated coupling table. If the intravenous tube is different from the one that was being used until now, the result is judged as an error. As already described, by reading IC tags together in all joint parts again, it can be verified whether the instillation apparatus is set up correctly, which leads to improved prevention of medical malpractice.

In step (5), the nurse opens the intravenous probe and resumes the instillation, then presses the step finish button.

As above, even in drug container replacement for the same drug, by reading the IC tags together in the joint part, medical malpractice can be detected. Furthermore, the order tables are updated in response to order change such as replacing the drug container with a container of another drug and instillation apparatus replacement and, hence, memory rewriting in IC tags is not needed. Thereby, medical staff can carry out work smoothly even in a case of order change. Although the above embodiments have been described with the example of instillation, the order is not limited to kinds of instillation.

Fourth Embodiment

In a forth embodiment, an example of IC tags that can be read only after coupling is done.

As in the second embodiment, the wristband of the patient and the intravenous tube are coupled, but the wristband F3 is fitted with a hook-and-loop fastener F1 as a coupling means, as shown in FIG. 11. One end of the hook-and-loop fastener F1 is basically fixed to a position "a" on the wristband F3 and an IC tag T1 is attached to the reverse side of the hook-and-loop fastener F1. As a metallic film material is put inside the hook-and-loop fastener F1, it is impossible to read the IC tag in this state. When the intravenous tube F2 is coupled to the wristband, the intravenous tube F2 is put on the wristband F3, the hook-and-loop fastener F1 is separated from the position "a", reversed so as to extend over the intravenous tube F2, and fixed to a position "b". The position of the wristband F3 is adjusted so that the IC tag T2 on the intravenous tube F2 comes very close to the hook-and-loop fastener F1. Because the hook-and-loop fastener F1 is reversed, it becomes possible to read the IC tag T1 and it becomes possible to read the IC tag T2 on the intravenous tube F2, the IC tag on the hook-and-loop fastener F1, and the IC tag T3 on the wristband together.

If a fixing element that is movable for coupling is provided, IC tag reading becomes possible only after the fixing element is moved after coupling is done. For example, as illustrated in FIG. 12, in a case where a component 1 (G1) and a component 2 (G2) are coupled and these components are locked up by sliding a fixing element G3 provided on the component 1 (G1), an IC tag TG2 on the component 1 (G1) that cannot be read as it is under the fixing element G3 before sliding becomes readable after sliding. If an IC tag TG3 on the component 2 (G2) is positioned so as to be close to the IC tag TG2, the IC tag TG3 and the IC tag TG2 can be read together.

In this way, by using a movable fixing element and using IC tags that become movable only after moving the fixing element, the possibility of reading the IC tags before coupling because of erroneous operation by a nurse is eliminated. Consequently, it can be verified for sure whether components are coupled correctly and medical malpractice can be prevented.

Although the examples in the medical sector have been discussed in the second to fourth embodiments, it goes without saying that application of the invention is not limited to the medical sector.

It will be understood by those skilled in the art that the present invention is not limited to the embodiments described herein, rather various modifications may be made and the described embodiments may be combined appropriately.

The present invention can be utilized for assembly work supporting system that relates to the management of assembly work including coupling plural components and detects whether the components are coupled correctly using IC tags.

What is claimed is:

1. A method for supporting assembly work that comprises coupling a plurality of components to which IC tags are attached respectively using a system that comprises a terminal connected to a server via a network, the terminal including an IC tag reading unit, a display and messaging unit, and a control communication unit, wherein information representing mating relations between the IC tags and joint parts of the plurality of components to which the IC tags are attached is stored in the terminal, the method comprising:
   after coupling a first component and a second component, using the IC tag reading unit to read a first IC tag attached to a joint part of the first component and a second IC tag attached to a joint part of the second component together in a manner of preventing collision;
   using the control communication unit to determine whether the first component and the second component are coupled correctly, based on identification data for the first IC tag and identification data for the second IC tag which have been read together and the information representing the mating relations between the IC tags and the joint parts of the plurality of components; and
   displaying a result of determining whether the first component and the second component are coupled correctly on the display and messaging unit of the terminal, and wherein, if a number of IC tags which have been read together exceeds a first predetermined threshold value, a coupling of the first component and the second component is determined by the control communication unit to be incorrect.

2. The method for supporting assembly work according to claim 1, wherein, after coupling the plurality of components, IC tags attached to joint parts of the components are read together in each joint part using the IC tag reading unit and, if a total number of the IC tags which have been read exceeds a second predetermined threshold value, the assembly work is determined to be incorrect.

3. The method for supporting assembly work according to claim 1, wherein the first IC tag or the second IC tag becomes readable after the first component and the second component are coupled.

4. The method for supporting assembly work according to claim 1, wherein the information representing the mating relations between the IC tags and joint parts of the plurality of components to which the IC tags are attached is received from the server for pre-storing in the terminal.

5. A system for supporting assembly work that comprises coupling a plurality of components, the system comprising:
   a terminal and a server,
   the terminal including:
   an IC tag reading unit that reads a first IC tag and a second IC tag together in a manner of preventing collision, the first and second IC tags being attached to respective joint parts of a first component and a second component of the plurality of components that have been coupled;
   a control communication unit that sends identification data for the first IC tag and identification data for the second IC tag which have been read together to the server via a network; and
   a display and messaging unit,
   the server including:
   a memory that stores information representing mating relations between IC tags and joint parts of the plurality of components to which the IC tags are attached; and
   a system control unit that receives the identification data for the first IC tag and the identification data for the second IC tag and determines whether the first component and the second component are coupled correctly, based on the information representing the mating relations of the IC tags, and wherein
   the system control unit sends a result of determining whether the first component and the second component are coupled correctly to the terminal, and
   the display and messaging unit of the terminal displays the result of determining whether the first component and the second component are coupled correctly.

6. The system for supporting assembly work according to claim 5, wherein the system control unit determines a coupling of the first component and the second component to be incorrect if a number of IC tags which have been read together exceeds a predetermined threshold value.

7. The system for supporting assembly work according to claim 5, wherein the system control unit determines the assembly work to be incorrect, if a total number of the IC tags which have been read together in each joint part after coupling the plurality of components exceeds a predetermined threshold value.

8. The system for supporting assembly work according to claim 5, wherein the first IC tag or the second IC tag becomes readable after the first component and the second component are coupled.

9. A system for supporting assembly work that comprises coupling a plurality of components, the system comprising:
   a server; and
   a terminal that includes an IC tag reading unit, a display and messaging unit, and a control communication unit, the terminal storing information representing mating relations between IC tags and joint parts of the plurality of components to which the IC tags are attached, and wherein
   after coupling a first component and a second component, the IC tag reading unit reads a first IC tag and a second IC tag together in a manner of preventing collision, the first and second IC tags being attached to respective joint parts of a first component and a second component of the plurality of components that have been coupled,
   the control communication unit receives identification data for the first IC tag and identification data for the second IC tag which have been read together and determines whether the first component and the second component are coupled correctly based on the identification data for the first IC tag, the identification data for the second IC tag, and the information representing the mating relations between the IC tags and the joint parts of the plurality of components, and
   the display and messaging unit of the terminal displays a result of determining whether the first component and the second component are coupled correctly, and
   wherein the control communication unit determines the coupling of the first component and the second component to be incorrect if a number of IC tags that have been read together exceeds a first predetermined threshold value.

10. The system for supporting assembly work according to claim 9, wherein the control communication unit determines the assembly work to be incorrect if a total number of the IC tags which have been read together in each joint part after coupling the plurality of components exceeds a second predetermined threshold value.

11. The system for supporting assembly work according to claim 9, wherein the first IC tag or the second IC tag becomes readable after the first component and the second component are coupled.

\* \* \* \* \*